US010232033B2

United States Patent
Yan et al.

(10) Patent No.: US 10,232,033 B2
(45) Date of Patent: Mar. 19, 2019

(54) RESPIRATORY SYNCYTIAL VIRUS VACCINE

(71) Applicant: Wuhan Sanli BioTechnology Company Limited, Wuhan (CN)

(72) Inventors: Huimin Yan, Wuhan (CN); Jingyi Yang, Wuhan (CN); Bali Zhao, Wuhan (CN)

(73) Assignee: Wuhan Sanli BioTechnology Company Limited, Wuhan (CN)

( * ) Notice: Subject to any disclaimer, the term of this patent is extended or adjusted under 35 U.S.C. 154(b) by 0 days.

(21) Appl. No.: 15/765,268

(22) PCT Filed: Oct. 31, 2016

(86) PCT No.: PCT/CN2016/104026
§ 371 (c)(1),
(2) Date: Apr. 1, 2018

(87) PCT Pub. No.: WO2018/076342
PCT Pub. Date: May 3, 2018

(65) Prior Publication Data
US 2019/0000962 A1    Jan. 3, 2019

(51) Int. Cl.
| | | |
|---|---|---|
| *A61K 39/00* | (2006.01) | |
| *C07H 21/04* | (2006.01) | |
| *C07K 14/195* | (2006.01) | |
| *A61K 39/12* | (2006.01) | |
| *C07K 5/00* | (2006.01) | |
| *A61K 39/155* | (2006.01) | |
| *C12N 7/00* | (2006.01) | |
| *A61P 11/00* | (2006.01) | |
| *A61P 31/14* | (2006.01) | |

(52) U.S. Cl.
CPC ............ *A61K 39/155* (2013.01); *A61P 11/00* (2018.01); *A61P 31/14* (2018.01); *C12N 7/00* (2013.01); *C12N 2760/18534* (2013.01); *C12N 2760/18551* (2013.01)

(58) Field of Classification Search
CPC ............... A61K 2300/00; A61K 39/00; A61K 2039/53; A61K 31/7052; C07K 14/315
See application file for complete search history.

(56) References Cited

PUBLICATIONS

Cullen LM et al. Cotton rat immune responses to virus-like particles containing the pre-fusion form of respiratory syncytial virus fusion . . . J Transl Med. Nov. 5, 2015; 13:350.
Delgado MF et al. Lack of antibody affinity maturation due to poor Toll-like receptor stimulation leads to enhanced respiratory syncytial virus . . . Nat Med. Jan. 2009;15(1):34-41.
Green CA et al. Chimpanzee adenovirus- and MVA-vectored respiratory syncytial virus vaccine is safe and immunogenic in adults. Sci Transl Med. 7:300ra126 (2015).
Groothuis JR et al.Safety and immunogenicity of a purified f protein respiratory syncytial virus (pfp-2) vaccine in seropositive children . . . J Infect Diseases 1998; 177(2):467.
Hagglund S et al. Characterization of an experimental vaccine for bovine respiratory syncytial virus. Clin Vaccine Immunol. 21: 997-1004 (2014).
Kim KH et al. Alum adjuvant enhances protection against respiratory syncytial virus but exacerbates pulmonary inflammation . . . PLOS ONE. 10: e0139916 (2015).
Lee S et al. Additive protection induced by mixed virus-like particles presenting respiratory syncytial virus fusion or attachment . . . Antiviral Res. Nov. 2014;111:129-35.
Schepens B et al. Protection and mechanism of action of a novel human respiratory syncytial virus vaccine candidate based on . . . EMBO Mol Med. Oct. 8, 2014;6(11):1436-54.
Yang K et al. Mucosal vaccines against respiratory syncytial virus. Curr Opin Virol. 6:78-84 (2014).

*Primary Examiner* — Barry A Chestnut
(74) *Attorney, Agent, or Firm* — Guangzhou YIHE IP Service

(57) ABSTRACT

A respiratory syncytial virus (RSV) vaccine comprising a recombinant fusion protein antigen. In one embodiment, the recombinant fusion protein antigen comprises a phosphoprotein (P) moiety, wherein the P moiety is a polypeptide that shares at least 90% identity to the polypeptide represented by SEQ ID NO 2 or SEQ ID NO 4; and a flagellin moiety, wherein the flagellin moiety is a polypeptide that shares at least 90% identity to the polypeptide represented by SEQ ID NO 8; whereby the P moiety and flagellin moiety are covalently coupled so as to form a linear polypeptide.

10 Claims, 14 Drawing Sheets
Specification includes a Sequence Listing.

ATGGGCAGCAGCCATCATCATCATCATCACAGCAGCGGCCTGGTGCCGCGCGGCAGCCATAT
GGCTAGCATGGAAAAGTTCGCGCCTGAATTCCATGGAGAAGATGCAAACAACAGGGCTACTA
AATTCCTAGAATCAATAAAGGGCAAATTCACATCACCCAAAGATCCCAAGAAAAAGATAGTAT
CATATCTGTCAACTCAATAGATATAGAAGTAACCAAAGAAAGCCCTATAACATCAAATTCAACTA
TTATCAACCCAACAAATGAGACAGATGATACTGCAGGGAACAAGCCCAATTATCAAAGAAAAC
CTCTAGTAAGTTTCAAAGAAGACCCTACACCAAGTGATAATCCCTTTTCTAAACTATACAAAGA
AACCATAGAAACATTTGATAACAATGAAGAAGAATCCAGCTATTCATACGAAGAAATAAATGAT
CAGACAAACGATAATATAACAGCAAGATTAGATAGGATTGATGAAAAATTAAGTGAAATACTAG
GAATGCTTCACACATTAGTAGTGGCAAGTGCAGGACCTACATCTGCTCGGGATGGTATAAGAG
ATGCCATGGTTGGTTTAAGAGAAGAAATGATAGAAAAAATCAGAACTGAAGCATTAATGACCA
ATGACAGATTAGAAGCTATGGCAAGACTCAGGAATGAGGAAAGTGAAAAGATGGCAAAAGA
CACATCAGATGAAGTGTCTCTCAATCCAACATCAGAGAAATTGAACAACCTATTGGAAGGGAA
TGATAGTGACAATGATCTATCACTTGAAGATTTTAAGCTTGCGGGCGCACTCGAG (a)

MGSSHHHHHHSSGLVPRGSHMASMEKFAPEFHGEDANNRATKFLESIKGKFTSPKDPKKKDSII
SVNSIDIEVTKESPITSNSTIINPTNETDDTAGNKPNYQRKPLVSFKEDPTPSDNPFSKLYKETIETFD
NNEEESSYSYEEINDQTNDNITARLDRIDEKLSEILGMLHTLVVASAGPTSARDGIRDAMVGLREE
MIEKIRTEALMTNDRLEAMARLRNEESEKMAKDTSDEVSLNPTSEKLNNLLEGNDSDNDLSLED
FKLAGALE (b)

ATGGAAAAGTTCGCGCCTGAATTCCATGGAGAAGATGCAAACAACAGGGCTACTAAATTCCTA
GAATCAATAAAGGGCAAATTCACATCACCCAAAGATCCCAAGAAAAAGATAGTATCATATCTG
TCAACTCAATAGATATAGAAGTAACCAAAGAAAGCCCTATAACATCAAATTCAACTATTATCAAC
CCAACAAATGAGACAGATGATACTGCAGGGAACAAGCCCAATTATCAAAGAAAACCTCTAGTA
AGTTTCAAAGAAGACCCTACACCAAGTGATAATCCCTTTTCTAAACTATACAAAGAAACCATAG
AAACATTTGATAACAATGAAGAAGAATCCAGCTATTCATACGAAGAAATAAATGATCAGACAAA
CGATAATATAACAGCAAGATTAGATAGGATTGATGAAAAATTAAGTGAAATACTAGGAATGCTT
CACACATTAGTAGTGGCAAGTGCAGGACCTACATCTGCTCGGGATGGTATAAGAGATGCCATG
GTTGGTTTAAGAGAAGAAATGATAGAAAAAATCAGAACTGAAGCATTAATGACCAATGACAGA
TTAGAAGCTATGGCAAGACTCAGGAATGAGGAAAGTGAAAAGATGGCAAAAGACACATCAG
ATGAAGTGTCTCTCAATCCAACATCAGAGAAATTGAACAACCTATTGGAAGGGAATGATAGTG
ACAATGATCTATCACTTGAAGATTTT (c)

FIG 1

MEKFAPEFHGEDANNRATKFLESIKGKFTSPKDPKKKDSIISVNSIDIEVTKESPITSNSTIINPTNET
DDTAGNKPNYQRKPLVSFKEDPTPSDNPFSKLYKETIETFDNNEEESSYSYEEINDQTNDNITARLD
RIDEKLSEILGMLHTLVVASAGPTSARDGIRDAMVGLREEMIEKIRTEALMTNDRLEAMARLRNE
ESEKMAKDTSDEVSLNPTSEKLNNLLEGNDSDNDLSLEDF (d)

ATGGGCAGCAGCCATCATCATCATCATCACAGCAGCGGCCTGGTGCCGCGCGGCAGCCATAT
GGCTAGCATGGAAAAGTTCGCGCCTGAATTCCATGGAGAAGATGCAAACAACAGGGCTACTA
AATTCCTAGAATCAATAAAGGGCAAATTCACATCACCCAAAGATCCCAAGAAAAAGATAGTAT
CATATCTGTCAACTCAATAGATATAGAAGTAACCAAAGAAAGCCCTATAACATCAAATTCAACTA
TTATCAACCCAACAAATGAGACAGATGATACTGCAGGGAACAAGCCCAATTATCAAAGAAAAC
CTCTAGTAAGTTTCAAAGAAGACCCTACACCAAGTGATAATCCCTTTTCTAAACTATACAAAGA
AACCATAGAAACATTTGATAACAATGAAGAAGAATCCAGCTATTCATACGAAGAAATAAATGAT
CAGACAAACGATAATATAACAGCAAGATTAGATAGGATTGATGAAAAATTAAGTGAAATACTAG
GAATGCTTCACACATTAGTAGTGGCAAGTGCAGGACCTACATCTGCTCGGGATGGTATAAGAG
ATGCCATGGTTGGTTTAAGAGAAGAAATGATAGAAAAAATCAGAACTGAAGCATTAATGACCA
ATGACAGATTAGAAGCTATGGCAAGACTCAGGAATGAGGAAAGTGAAAAGATGGCAAAAGA
CACATCAGATGAAGTGTCTCTCAATCCAACATCAGAGAAATTGAACAACCTATTGGAAGGGAA
TGATAGTGACAATGATCTATCACTTGAAGATTTTAAGCTTGCGGGCGCACTCGAGCACCACCA
CCACCACCACTGA (e)

MGSSHHHHHHSSGLVPRGSHMASMEKFAPEFHGEDANNRATKFLESIKGKFTSPKDPKKKDSII
SVNSIDIEVTKESPITSNSTIINPTNETDDTAGNKPNYQRKPLVSFKEDPTPSDNPFSKLYKETIETFD
NNEEESSYSYEEINDQTNDNITARLDRIDEKLSEILGMLHTLVVASAGPTSARDGIRDAMVGLREE
MIEKIRTEALMTNDRLEAMARLRNEESEKMAKDTSDEVSLNPTSEKLNNLLEGNDSDNDLSLED
FKLAGALEHHHHHH (f)

FIG 1 (cont'd)

ATGGCACAAGTCATTAATACCAACAGCCTCTCGCTGATCACTCAAAATAATATCAACAAGAACC
AGTCTGCGCTGTCGAGTTCTATCGAGCGTCTGTCTTCTGGCTTGCGTATTAACAGCGCGAAGG
ATGACGCAGCGGGTCAGGCGATTGCTAACCGTTTCACCTCTAACATTAAAGGCCTGACTCAGG
CGGCCCGTAACGCCAACGACGGTATCTCCGTTGCGCAGACCACCGAAGGCGCGCTGTCCGAA
ATCAACAACAACTTACAGCGTGTGCGTGAACTGACGGTACAGGCCACTACCGGTACTAACTCT
GAGTCTGATCTGTCTTCTATCCAGGACGAAATTAAATCCCGTCTGGATGAAATTGACCGCGTAT
CTGGTCAGACCCAGTTCAACGGCGTGAACGTGCTGGCAAAAAATGGCTCCATGAAAATCCAG
GTTGGCGCAAATGATAACCAGACTATCACTATCGATCTGAAGCAGATTGATGCTAAAACTCTTG
GCCTTGATgctagcgctacgacgacGGATCCGCTGAAAGCGCTGGACGATGCTATCGCATCTGTAGA
CAAATTCCGTTCTTCCCTCGGTGCGGTGCAAAACCGTCTGGATTCCGCGGTTACCAACCTGAA
CAACACCACTACCAACCTGTCTGAAGCGCAGTCCCGTATTCAGGACGCCGACTATGCGACCGA
AGTGTCCAATATGTCGAAAGCGCAGATCATCCAGCAGGCCGGTAACTCCGTGTTGGCAAAAG
CTAACCAGGTACCGCAGCAGGTTCTGTCTCTGCTGCAGGGT (g)

MAQVINTNSLSLITQNNINKNQSALSSSIERLSSGLRINSAKDDAAGQAIANRFTSNIKGLTQAAR
NANDGISVAQTTEGALSEINNNLQRVRELTVQATTGTNSESDLSSIQDEIKSRLDEIDRVSGQTQF
NGVNVLAKNGSMKIQVGANDNQTITIDLKQIDAKTLGLDASATTTDPLKALDDAIASVDKFRSSL
GAVQNRLDSAVTNLNNTTTNLSEAQSRIQDADYATEVSNMSKAQIIQQAGNSVLAKANQVPQ
QVLSLLQG (h)

FIG 1 (cont'd)

ATGGGCAGCAGCCATCATCATCATCATCACAGCAGCGGCCTGGTGCCGCGCGGCAGCC*ATAT*
*GGCTAGC*ATGGAAAAGTTCGCGCCTGAATTCCATGGAGAAGATGCAAACAACAGGGCTACTA
AATTCCTAGAATCAATAAAGGGCAAATTCACATCACCCAAAGATCCCAAGAAAAAGATAGTAT
CATATCTGTCAACTCAATAGATATAGAAGTAACCAAAGAAAGCCCTATAACATCAAATTCAACTA
TTATCAACCCAACAAATGAGACAGATGATACTGCAGGGAACAAGCCCAATTATCAAAGAAAAC
CTCTAGTAAGTTTCAAAGAAGACCCTACACCAAGTGATAATCCCTTTTCTAAACTATACAAAGA
AACCATAGAAACATTTGATAACAATGAAGAAGAATCCAGCTATTCATACGAAGAAATAAATGAT
CAGACAAACGATAATATAACAGCAAGATTAGATAGGATTGATGAAAAATTAAGTGAAATACTAG
GAATGCTTCACACATTAGTAGTGGCAAGTGCAGGACCTACATCTGCTCGGGATGGTATAAGAG
ATGCCATGGTTGGTTTAAGAGAAGAAATGATAGAAAAAATCAGAACTGAAGCATTAATGACCA
ATGACAGATTAGAAGCTATGGCAAGACTCAGGAATGAGGAAAGTGAAAAGATGGCAAAAGA
CACATCAGATGAAGTGTCTCTCAATCCAACATCAGAGAAATTGAACAACCTATTGGAAGGGAA
TGATAGTGACAATGATCTATCACTTGAAGATTTCGGG*GCGCC*ATGGCACAAGTCATTAATACC
AACAGCCTCTCGCTGATCACTCAAAATAATATCAACAAGAACCAGTCTGCGCTGTCGAGTTCTA
TCGAGCGTCTGTCTTCTGGCTTGCGTATTAACAGCGCGAAGGATGACGCAGCGGGTCAGGCG
ATTGCTAACCGTTTCACCTCTAACATTAAAGGCCTGACTCAGGCGGCCCGTAACGCCAACGAC
GGTATCTCCGTTGCGCAGACCACCGAAGGCGCGCTGTCCGAAATCAACAACAACTTACAGCG
TGTGCGTGAACTGACGGTACAGGCCACTACCGGTACTAACTCTGAGTCTGATCTGTCTTCTATC
CAGGACGAAATTAAATCCCGTCTGGATGAAATTGACCGCGTATCTGGTCAGACCCAGTTCAAC
GGCGTGAACGTGCTGGCAAAAAATGGCTCCATGAAAATCCAGGTTGGCGCAAATGATAACCA
GACTATCACTATCGATCTGAAGCAGATTGATGCTAAAACTCTTGGCCTTGAT*gctagcgctacgacga*
*c*GGATCCGCTGAAAGCGCTGGACGATGCTATCGCATCTGTAGACAAATTCCGTTCTTCCCTCGG
TGCGGTGCAAAACCGTCTGGATTCCGCGGTTACCAACCTGAACAACACCACTACCAACCTGTC
TGAAGCGCAGTCCCGTATTCAGGACGCCGACTATGCGACCGAAGTGTCCAATATGTCGAAAGC
GCAGATCATCCAGCAGGCCGGTAACTCCGTGTTGGCAAAAGCTAACCAGGTACCGCAGCAGG
TTCTGTCTCTGCTGCAGGGT*ctcgagcaccaccaccaccaccac*TGA (i)

MGSSHHHHHHSSGLVPRGSHMAS MEKFAPEFHGEDANNRATKFLESIKGKFTSPKDPKKKDSII
SVNSIDIEVTKESPITSNSTIINPTNETDDTAGNKPNYQRKPLVSFKEDPTPSDNPFSKLYKETIETFD
NNEEESSYSYEEINDQTNDNITARLDRIDEKLSEILGMLHTLVVASAGPTSARDGIRDAMVGLREE
MIEKIRTEALMTNDRLEAMARLRNEESEKMAKDTSDEVSLNPTSEKLNNLLEGNDSDNDLSLED
FGRA MAQVINTNSLSLITQNNINKNQSALSSSIERLSSGLRINSAKDDAAGQAIANRFTSNIKGLT
QAARNANDGISVAQTTEGALSEINNNLQRVRELTVQATTGTNSESDLSSIQDEIKSRLDEIDRVSG
QTQFNGVNVLAKNGSMKIQVGANDNQTITIDLKQIDAKTLGLDASATTTDPLKALDDAIASVDK
FRSSLGAVQNRLDSAVTNLNNTTTNLSEAQSRIQDADYATEVSNMSKAQIIQQAGNSVLAKANQ
VPQQVLSLLQGLEHHHHHH (j)

FIG 1 (cont'd)

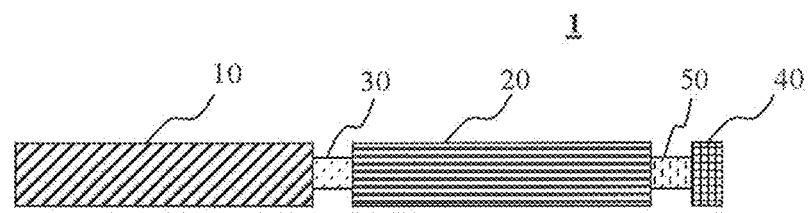
(a)
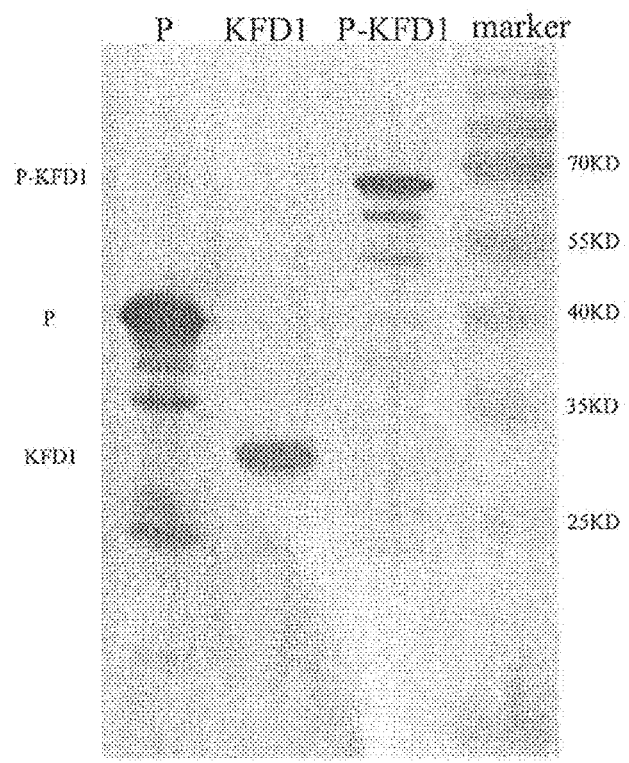
(b)
FIG 2

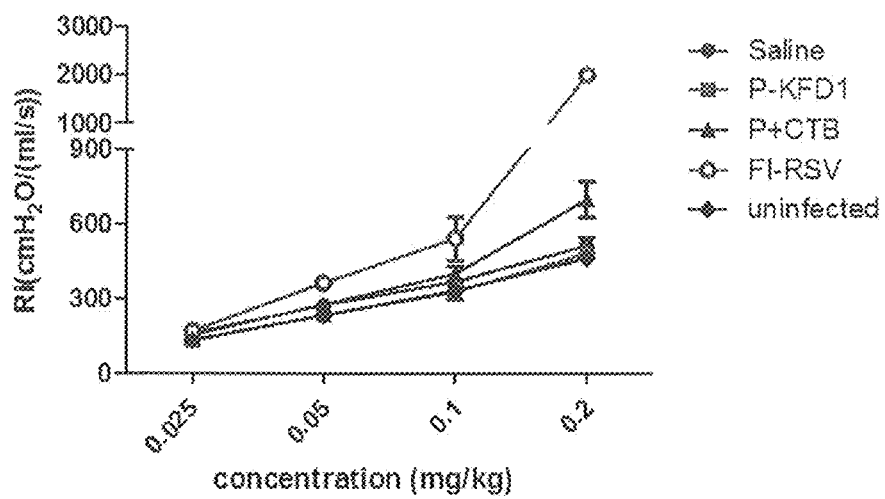
(a)
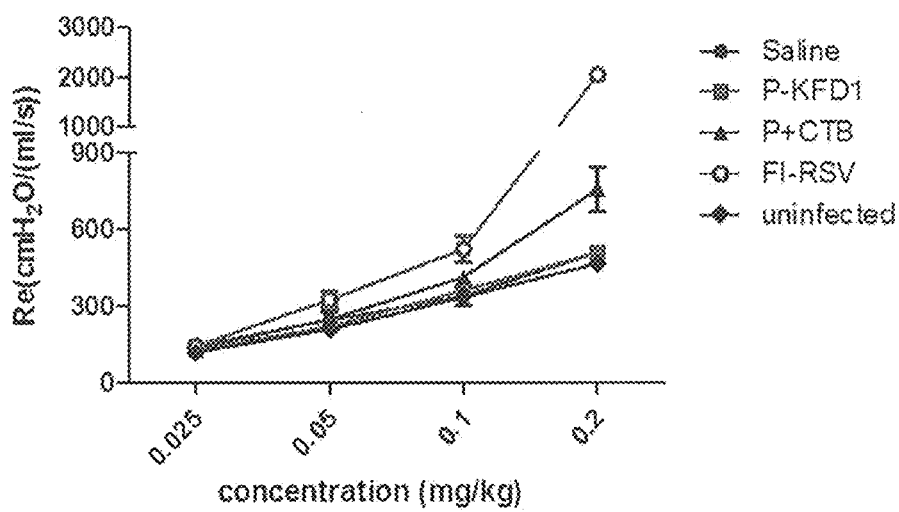
(b)
FIG 9

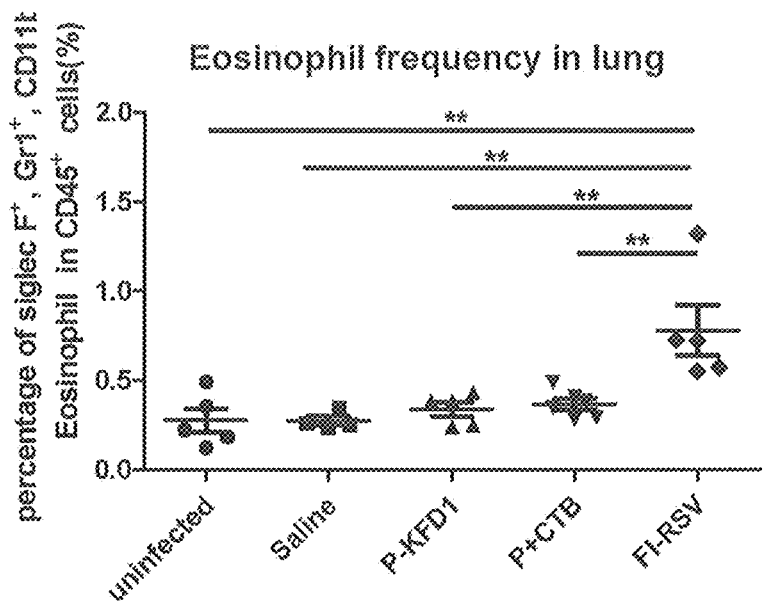
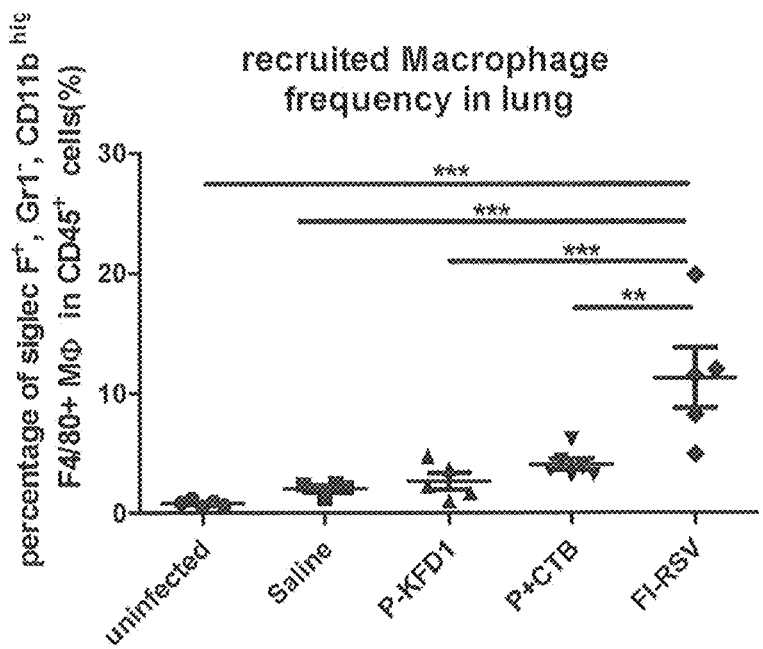
FIG 10 (cont'd)

RESPIRATORY SYNCYTIAL VIRUS VACCINE

FIELD OF THE INVENTION

The present invention generally relates to prophylactic and therapeutic agents against respiratory syncytial virus (RSV), and more particularly to a RSV vaccine comprising a recombinant fusion protein antigen containing phophoprotein (P) protein.

BACKGROUND OF THE INVENTION

Respiratory syncytial virus (RSV) is a leading cause for bronchiolitis and severe respiratory disease in infants, young children, immune-compromised and elderly populations worldwide. Natural RSV infection in young children does not elicit long-lasting immunity and individuals remain susceptible to repeated RSV infections throughout life. A formalin-inactivated RSV (FI-RSV) vaccine, tested in infants a half century ago, resulted in enhanced morbidity and two deaths after a subsequent exposure to a natural RSV infection. The infants and children that received the FI-RSV vaccine exhibited a lower level of neutralizing antibodies following a natural infection (Yang and Varga, 2014).

While much efforts and resources have been devoted to the development of a safe and effective RSV vaccine, there is no licensed RSV vaccine available so far. The researches carried out so far demonstrated that it is a daunting challenge for developing a safe and effective RSV vaccine.

Therefore, there is an imperative need to explore new ways to develop a safe and effective vaccine against RSV.

SUMMARY OF THE INVENTION

The present invention provides a respiratory syncytial virus (RSV) vaccine comprising a recombinant fusion protein antigen. In one embodiment, the recombinant fusion protein antigen comprises a phosphoprotein (P) moiety, wherein the P moiety is a polypeptide that shares at least 90% identifty to the polypeptide represented by SEQ ID NO 2 or SEQ ID NO 4; and a flagellin moiety, wherein the flagellin moiety is a polypeptide that shares at least 90% identity to the polypeptide represented by SEQ ID NO 8; whereby the P moiety and flagellin moiety are covalently coupled so as to form a linear polypeptide.

In another embodiment of the RSV vaccine, the P moiety is a polypeptide that shares at least 98% identity to the polypeptide represented by SEQ ID NO 2 or SEQ ID NO 4; and the flagellin moiety is a polypeptide that shares at least 98% identity to the polypeptide represented by SEQ ID NO 8.

In another embodiment of the RSV vaccine, the P moiety is a polypeptide that shares at least 99% identity to the polypeptide represented by SEQ ID NO 2 or SEQ ID NO 4; and the flagellin moiety is a polypeptide that shares at least 99% identity to the polypeptide represented by SEQ ID NO 8.

In another embodiment of the RSV vaccine, the P moiety is a polypeptide represented by SEQ ID NO 2 or SEQ ID NO 4; and the flagellin moiety is a polypeptide represented by SEQ ID NO 8.

In another embodiment of the RSV vaccine, the recombinant fusion protein antigen further comprises a first linker coupling the P moiety and flagellin moiety; wherein the first linker is an amino acid or a peptide of two to fifteen amino acids.

In another embodiment of the RSV vaccine, the recombinant fusion protein antigen further comprises a purification tag for facilitating the purification of the recombinant fusion protein antigen, wherein the purification tag is disposed at either the N-terminal or C-terminal of the recombinant fusion protein antigen. In further embodiment, the purification tag is composed of six histidine residues. In yet another embodiment, the recombinant fusion protein antigen further comprises a second linker linearly coupling the purification tag with the P moiety or flagellin moiety. In yet further embodiment, the second linker is a cleavable linker that is composed of an amino acid or a sequence of amino acids which can be cleaved chemically or enzymatically at its C-terminal.

In another embodiment of the RSV vaccine, the recombinant fusion protein antigen is represented by SEQ ID NO 10.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will new be described with reference to the Figures, in which like reference numerals denote like elements.

FIG. 1 shows the sequences:
(a) SEQ ID NO 1, nucleotide sequence of RSV A2 strain P protein;
(b) SEQ OD NO 2, amino acid sequence of RSV A2 strain P protein;
(c) SEQ ID NO 3, nucleotide sequence of RSV mutant cpt-248 P protein;
(d) SEQ ID NO 4, amino acid sequence of RSV mutant cpt-248 P protein;
(e) SEQ ID NO 5, nucleotide sequence of recombinant P protein with His tag underline;
(f) SEQ ID NO 6, amino acid sequence of recombinant P protein with His tag, where the RSV mutant cpt-248 P protein as shown as SEQ ID NO 4 is underlined, and the His tag is bolded;
(g) SEQ ID NO 7, nucleotide sequence of recombinant flagellin KFD1;
(H) SEQ ID NO 8, amino acid sequence of recombinant flagellin KFD1;
(i) SEQ ID NO 9, nucleotide sequence of recombinant P-KFD1, where the RSV mutant cpt-248 protein as shown as SEQ ID NO 3 is underlined, the nucleotide sequence of SEQ ID NO 7 is double underlined, and the His tag is bolded;
(j) SEQ ID NO 10, amino acid sequence of recombinant P-KFD1, where the RSV mutant cpt-248 protein as shown as SEQ ID NO 4 is underlined, the amino acid sequence of SEQ ID NO 8 is double underlined, and the His tag is bolded.

FIG. 2(a) shows a schematic diagram of functional blocks in a recombinant P-KPD1 protein in accordance with one embodiment of the present invention; FIG. 2(b) shows a western blot of purified P-KFD1 protein.

FIG. 9 provides graphs: (a) showing the correlation of inspiratory resistance (RI) with different concentrations of methacholine (MCH); and (b) showing the correlation of expiratory resistance (RE) with different concentrations of methacholine (MCH) in different groups after challenge.

DETAILED DESCRIPTION OF THE INVENTION

Figure 3:
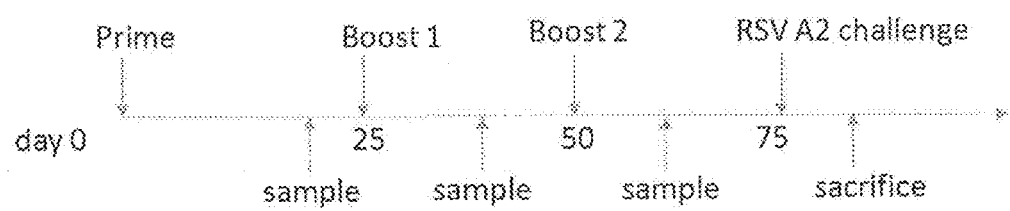
FIG. 3 shows a diagram of temporal protocol of immunization and challenge.

The present invention may be understood more readily by reference to the following detailed description of certain embodiments of the invention.

Throughout thus application, where publications are referenced, the disclosures of these publications are hereby incorporated by reference, in their entireties, into this application in order to more fully describe the state of art to which this invention pertains.

The practice of the present invention will employ unless otherwise indicated, conventional techniques of molecular biology (including recombinant techniques), microbiology, cell biology, biochemistry and immunology, which are within the skill of the art. Such techniques are explained fully in the literature, for example, *Molecular Cloning: A Laboratory Manual*, second edition (Sambrook and Russel, 2001); *Current Protocols in Molecular Biology* (F. M. Ausubel et al. eds., 1987).

RSV has a linear single-stranded RNA genome with 10 genes encoding 11 proteins, including non-structural proteins (NS1 and NS2), large polymerase (L), prosphoprotein (P) nucleocapsid (N), matrix protein (M), surface attachment glycoprotein (G), surface fusion glycoprotein (F), small hydrophic protein (SH), a transcription factor (M2-1) and an accessory protein (M2-2). G and F proteins have been considered the two major protective antigens for eliciting neutralizing antibodies. G protein is heavily glycosylated and involved in vital attachment to host cells, and F protein mediates cell fusion allowing entry of the virus into the cell cytoplasm and formation of syncytia (Yang and Varga 2014).

Since RSV F protein is a very important neutralizing antigen to potentially induce mucosal immunity, it has been the focus for development or an RSV vaccine. Based on the recent identification of the very potent neutralizing antigen site in the prefusion F, the next generation of RSV vaccine candidates should include the F protein expressed in the profusion form (Yang and Varga, 2014).

Because RSV infection is restricted to the respiratory tract, an RSV vaccine should elicit mucosal immunity at upper and lower respiratory tracts in order to most effectively prevent RSV reinfection (Yang and Varga, 2014). The efficient induction of mucosal immune responses requires appropriate administration routes and specific adjuvants and/or delivery systems intranasal delivery is the most effective route to induce potent and broad mucosal immune responses at multiple mucosal sites as compared to other mucosal delivery routes (Yang and Varga, 2014).

RSV vaccines have four main categories including inactivated, live-attenuated, gene-based vectors and subunit. Live-attenuated RSV vaccines administered intranasally, and a subunit RSV postfusion F protein vaccine adjuvanted with alum and delivered intramuscularly have been extensively evaluated in a number of clinical trials in recent years. However, the live-attenuated RSV vaccine induced a response that was weaker in magnitude than that of natural infection due to loss of immunogenicity during the process of attenuation (Yang and Varga, 2014).

Being delivered usually by systemic immunization, F protein-based RSV vaccines were proven safe in older children and adults, however their immunogenicity was modest and they failed to induce potent mucosal immunity (Groothuis J R, et al. 1998).

Antigen Selections

VLPs expressing F or G protein could confer protection against RSV challenge in mice, but VLP G vaccination enhanced disease when used alone; one interesting result was that mixed VLP F+VLP G were without vaccine induced immunopathology even though no plausible explanation was provided (Lee S. et al. 2014).

Chimpanzee adenovirus and modified vaccinia virus encoding RSV proteins F, N and M2-1 have been tested in phase 1 clinical trials (Green C. A., 2015).

VLP containing pre-fusion form F protein was tested in cotton rats for its protection against RSV (Cullen L. M., et al. 2015).

A peptide corresponding to the viral surface small hydrophobic (SH) ectodomain of HRSV B (CGGGS-NKLSEH-KTFSNKTLEQCQMYQINT) chemically conjugated to Hepatitis B core protein virus-like particles (HBc-SHeB) showed reducing viral replication in challenged mice and cotton rats (Schepens, B. et al 2014).

Adjuvant Selections

Alum-adjuvanted FI-RSV induced severe vaccine-enhanced RSV disease including weight loss, eosinophilia, and lung histopathology while it enhanced protection against RSV over unadjuvanted FI-RSV (Kim K H, et al. 2015).

Inactivated RSV adjuvanted with LPS. Poly(I:C), or PolyU induced protective immunity against live RSV challenge (Delgado M F, et al. 2009); however, all the adjuvants are chosen because of the components in RSV, i.e., F protein can activate TLR4 pathway like LPS; Poly(I:C) and PolyU function as viral genome.

Bovine RSV

Bovine RSV is a key player in the bovine respiratory disease complex, which is one of the most economically important and outstanding welfare issues in industrialized beef cattle production. The BRSV genome is very similar to the RSV genome (Hagglund S., et al. 2014).

When BRSV-immunostimulating complex (ISCOM) was used to immunize calves, IgG antibody specific for F, G, N, and SH are of high titers; it is to be noted that no significantly antibody responses against M and P were detected (Hagglund S., et al. 2014).

The present invention discovered a safe and effective RSV vaccine, where the vaccine comprises a recombinant fusion protein antigen. The recombinant fusion protein antigen comprises a phosphoprotein (P) moiety and a flagellin moiety, where the P moiety and flagellin moiety are covalently coupled so as to form a linear polypeptide. A "fusion protein" is a chimeric molecule in which the constituent moieties are all polypeptides and are attached (fused) to each other such that the chimeric molecule forms a continuous single chain. The various constituents can be directly attached to each other or can be coupled through one or more peptide linkers. A "linker" as used in reference to a chimeric molecule refers to any molecule that links or joins the constituent moieties of the chimeric molecule. Where the chimeric molecule is a fusion protein, the linker may be a peptide that joins the proteins comprising a fusion protein.

Referring now to FIG. 1, the exemplary sequences of P protein include RSV A2 strain (SEQ ID NO 1 for its nucleotide sequence and SEQ ID NO 2 for its amino acid sequence) and RSV mutant cpt-248 strain (SEQ ID NO 3 for its nucleotide sequence and SEQ ID NO 4 for its amino acid sequence). It is to be noted that P protein from RSV mutant cpt-248 strain shares 98-99% identity with that from other RSV A strains, and more than 90% identity with that from RSV B strains.

Referring now to FIG. 2(a), there is provided a schematic diagram of the functional blocks in the recombinant fusion protein antigen in accordance with one embodiment of the present invention. The recombinant protein antigen 1 comprises a phosphoprotein (P) moiety 10 and a flagellin moiety 20, where the P moiety 10 and flagellin moiety 20 are linearly covalent coupled. In certain embodiments, the flagellin moiety 20 uses its N-terminal to couple with the C terminal of the P moiety 10 (as shown in FIG. 2(a)). In certain embodiments, the flagellin moiety 20 uses its C-terminal to couple with the N-terminal of the P moiety 10 (switched positions in related to FIG. 2(a)).

In certain embodiments, the P moiety 10 is a polypeptide represented by SEQ ID NO 2 or SEQ ID NO 4. In certain embodiments, the P moiety 10 is a polypeptide that shares at least 90%, preferably 98%, even more preferably 99% identity to the polypeptide represented by SEQ ID NO 2 or SEQ ID NO 4.

In certain embodiments, the flagellin moiety 20 is a polypeptide represented by SEQ ID NO 8. In certain embodiments, the flagellin moiety 20 is a polypeptide that shares at least 90%, preferably 98%, even more preferably 99% identity to the polypeptide represented by SEQ ID NO 8.

In certain embodiments, the recombinant fusion protein antigen 1 further comprises a first linker 30 coupling the P moiety 10 and flagellin moiety 20, where the first linker 30 is an amino acid or a peptide of two or more amino acids, the amino acid(s) in the first linker 30 shall be flexible without large side residues to avoid immune responses. In addition, the first linker 30 shall be resistant to enzymatic digestion so as to stabilize the recombinant fusion protein antigen when such a vaccine is administrated.

In certain embodiments, the recombinant fusion protein antigen 1 further comprises a purification tag 40 for facilitating the purification of the recombinant fusion protein antigen 1. The purification tag 40 can be disposed at either the N-terminal or C-terminal of the recombinant fusion protein antigen 1. For example, six histidine residues are fusedly located at its N- or C-terminals, allowing purification using $Ni^{2+}$ column. After the purification, the six histidine residues can be removed by chemical or enzymatic cleavage. In fact, any known purification tag is suitable here including myc tag, HA tag, Flag-peptide, KT3 epitope, alpha-tubulin epitope, T7 gene 10 protein peptide tag, glutathione-S-transferase (GST), strep-tag, bovine pancreatic trypsin inhibitor (BPTI), and maltose binding protein (MBP).

In certain embodiments, the recombinant fusion protein antigen 1 further comprises a second linker 50 linearly coupling the purification tag 40 with the P moiety 10 or flagellin moiety 20. In certain embodiments, the second linker 50 is a cleavable linker that is composed of an ammo acid or a sequence of amino acids, which can be cleaved chemically or enzymatically at its C-terminal in the expression vectors, the cleavable linker comprises a DNA sequence which codes for an amino acid or a sequence of ammo acids which can be cleaved chemically or enzymatically at its C-terminal.

Examples of chemical agents useful for cleaving proteins are cyanogen bromide, 2-(2-nitrophenylsulfensyl)-3-bromo-3'-methylinolinium (BNPS-skatole), hydroxylamine, and the like. Cyanogen bromide cleaves proteins at the C-terminal of a methionine residue. BNPS-skatole cleaves at the C-terminal of a tryptophan residue. Hydroxylamine cleaves at the C-terminal of the moiety -Asn-Z— in which Z is Gly, Leu, or Ala.

Examples of enzymatic agents useful for cleavage are trypsin, papain, pepsin, plasmin, thrombin, enterokinase, and the like. Each effects cleavage at a particular amino acid sequence which it recognizes. Enterokinase, for example, recognizes the amino acid sequence -$(Asp)_n$-Lys- in which n is an integer from 2 to 4.

As discussed above, the techniques for expression vector cloning, construction and amplification are well known to those skilled in the art. Therefore, the expression vectors for the recombinant fusion protein antigen can be constructed by routine procedures; no further details are provided herein in order not to obscure the principles of the present invention.

The RSV vaccine of the present invention further comprises a pharmaceutically acceptable solution including such as saline, PBS. In certain embodiments, the RSV vaccine may include other components such as other proteins from RSV.

EXAMPLES

1. Preparation of Virus For Challenge

RSV stain A2 was propagated in Hep-2 cells; after sonication, centrifuged at 1000 g, 4° C. for 10 min; collected supernatants; ultra-centrifuged at 80,000 g, 4° C. for 2 hs to purify viruses. The purified viruses were titrated by plaque assay, and stored for challenges.

2. Preparation of FI-RSV

Added neutral formalin into purified RSV A2 virus suspension solution at 1:4,000, and incubated at 37° C. for 3 days with rotation; then centrifuged at 30,000 rpm for 30 min; the pellets were resuspended into a volume of 1/25 of the original volume; then mixed FI-RSV with adjuvant Alum (4 mg/ml) and incubated at room temperature for 24 hours.

3. Preparation of Recombinant Proteins

Referring now to FIG. 1, there are provided the sequences of recombinant P protein with His tag (nucleotide sequence of SEQ ID NO 5 and amino acid sequence of SEQ ID NO 6), recombinant flagellin KFD1 (nucleotide sequence of SEQ ID NO 7 and amino acid sequence of SEQ ID NO 8) and recombinant P-KFD1 (nucleotide sequence of SEQ ID NO 9 and amino acid sequence of SEQ ID NO 10). The DNA fragments were cloned into pET28a vector using primers (SEQ ID NOS 11-16), and the resultant pET28a-P, pET28a-KFD1, and pET28a-P-KFD1 expression plasmids were transformed into bacteria following conventional protocols. All expression recombinant proteins were verified by western blot (FIG. 2(b)) and purified using then His tag. Endotoxins were removed before use.

Immunization

Referring now to FIG. 3, there are provided the temporal protocols of immunization and manipulations. Groups of BALB/c mice (n=18) were immunized three times at days 0, 25 or 50; (a) 10 μl saline (i.n); (c) 10 μl P protein (40 μg) and 2 μl CTB adjuvant (2 μg, Sigma) mixture (i.n); (d) 12 μl P-KFD1 protein (24 μg) (i.n). For group (b), they were first immunized at day 42 and boosted two weeks later, 100 μl FI-RSV vaccine containing 2 μg FI-RSV and 400 μg alum adjuvant (i.m). Sera were collected at days 21, 39 or 64; the titers of neutralizing antibodies were assayed.

Challenge

Challenge was done at day 25 after the last immunization. All mice were anesthetized by Avertin (tribromoethanol dissolved in tert-pentyl alcohol), and i.n. infected with $1 \times 10^7$ PFU RSV A2 in a volume of 50 μl. The antigens and conditions for immunization and challenges are summarized in Table 1.

TABLE 1

Summary of antigens and conditions for immunization and challenges

| group | Number of mice | Route/dose | challenge doses | challenge volume |
|---|---|---|---|---|
| (a) Saline | 18 | i.n./saline-diluted anesthetic | $1*10^7$ PFU | 50 μl |
| (b) FI-RSV | 18 | i.m. at Day 42 (2×)/2 μg FI-RSV + 400 μg Alum | $1*10^7$ PFU | 50 μl |
| (c) P + CTB | 18 | i.n. (3×)/40 μg P + 2 μg CTB | $1*10^7$ PFU | 50 μl |
| (d) P-KFDI | 18 | i.n. (3×)/24 μg P-KFDI | $1*10^7$ PFU | 50 μl |

Immune Plaque Assay for Determining Virus Titers in Nasal and Lung Tissues

At day 4 post challenge, mice were sacrificed, and nose and lung tissues were collected, and homogenized using a homogenizer. In 24-well plates, Vero cells were inoculated, and grew into 100% confluence; then diluted homogenized samples were added into the wells, and incubated at 37° C. for 1 hour; after washing 3 times, added into wells 1 ml DMEM culture media containing 2% FBS, 1% P+S, 0.75% methyl cellulose; then incubated at an incubator for 4-5 days. Then, gently discarded culture media from the wells; fixed the wells with paraformaldehyde and Triton X-100 for 20 minutes; added P protein-specific monoclonal antibody; incubated for 2 hours; added Goat anti-mouse IgG-HRP; incubated for 1 hour, and finally developed with AEC substrate, and counted the plaques.

Titration of Serum Neutralization Antibody Titers

Sera were inactivated; then diluted sequentially at 2-fold, the diluted serum samples (100 μl) were incubated with 200 PFU of RSV A2 virus (100 μl) at 37° C. for 1 hours; then added onto Vero cell monolayer; allowed to adhere for 1 hour; incubated for 3 days; determined virus titers using immune plaque assay as described above. Serum neutralization antibody titer is defined as the serum inverse dilution folds that can cause a 50% reduction of plaque numbers, i.e. 50% plaque reduction neutralization titer (PRNT).

Measurement of Airway Responsiveness in Mice

Day 4 post-challenge, anesthetized the mice with pentobarbital sodium, cut open the neck skins of the mice with surgical scissors, stripped the trachea, inserted tracheal intubation into the stripped trachea, connected the other end of tracheal intubation to a ventilator, and set the respiration rate at 1.5:1, and ventilator passive respiratory frequency for 90 times/minute.

After that, the mice were quickly transferred to the volume scan box, and the trachea was connected with the airway of the volume scan box. Starting AniRes2005 operating software to observe the airway pressure change curve and adjusting air quantity to mice to the level at which mouse's spontaneous breathing could not resist the effects of ventilator passive respiratory. After the pressure change curve became smooth and regular, the skin and muscle of the neck side of the mouse were separated, and the vein puncture was carried out to fix the needle so as to establish an intravenous drug administration passage. After intravenous injection of methacholine (MCH) excitation at sequential concentrations of 0.025, 0.05, 0.1, 0.2 mgMCH/kg, used the analysis software to simultaneously record mouse airway inspiratory resistance (RI), expiratory resistance (RE) and pulmonary adaptation (cdyn) change curves.

Digestion of Lung Tissue

The mice were anesthetized with pentobarbital sodium, and the heart was perfused with 5 ml PBS from the right atrium. The lung tissue was separated and cut to 1-2 mm². The lung tissue was digested by 2 ml digestion buffer at 37° C. for 40 min. The formula of the digestion buffer. HBSS culture medium containing Collagenase I (125 U/ml) and DNase I (30 U/ml). After the digestion, the lung tissue was gently rubbed and filtered to obtain single cell suspension, and then separated by Percoll separation solution, so as to get the lymphocytes and mononuclear cells.

Flow Cytometry Method

For detecting various types of cell infiltration in the lung, cells were surface stained with the following specific monoclonal antibodies: FITC Anti-Mouse F4/80, PE-Cy7 Anti-Mouse Gr-1 APC-EF780 Anti-Mouse CD11b, APC Anti-Mouse CD45, PE Anti-Mouse Siglec F; the staining was at 4℉ for 30 min, and then the cells were fixed.

Analysis of T Cell Response Using ELISPOT Assay

At day 4 post challenge, the lung and spleen were taken, and lymphocytes were separated. Pre-coated IFN-γ ELISPOT plates after activation, were inoculated lung lymphocytes and spleen lymphocytes, and stimulated by P protein. The positive and negative controls were set up. Then the plates were incubated in the incubator for 48 hours, subsequently incubated with secondary antibody with AEC substrate color, with a multifunctional cell analysis and enzyme linked spot analysis system to compute plaques.

Histology

Lungs were fixed with formalin. After fixation, tissue sections were prepared following standard procedures. Some slides were stained with hematoxylin-eosin (H&E) to identify cellular infiltrates.

Results

Figure 4:
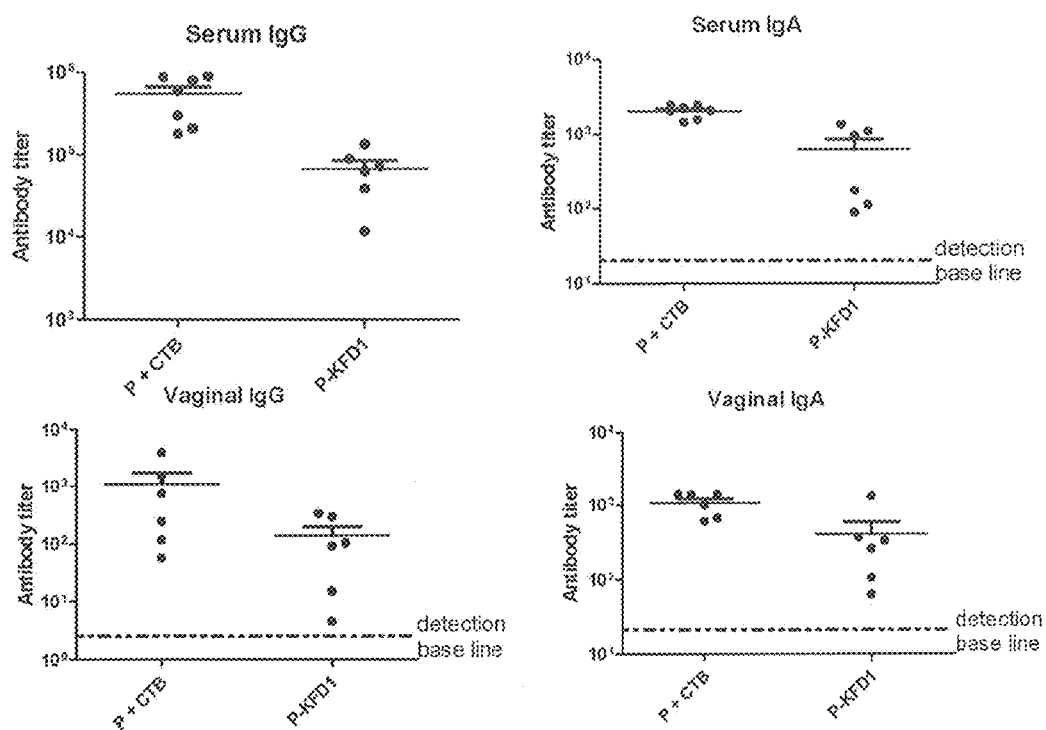
FIG. 4 provides graphs showing the P-specific IgG and IgA antibody titers in serum and vaginal samples from the groups of immunization with P+PCT or P-KFD1.

Referring now to FIG. 4, there are provided graphs showing the P-specific IgG and IgA antibody titers in serum and vaginal samples from the groups of immunization with P+CTB or P-KFD1. It is apparent that the group of immunization with P+CTB showed higher titers than the group of P-KFD1.

Figure 5:
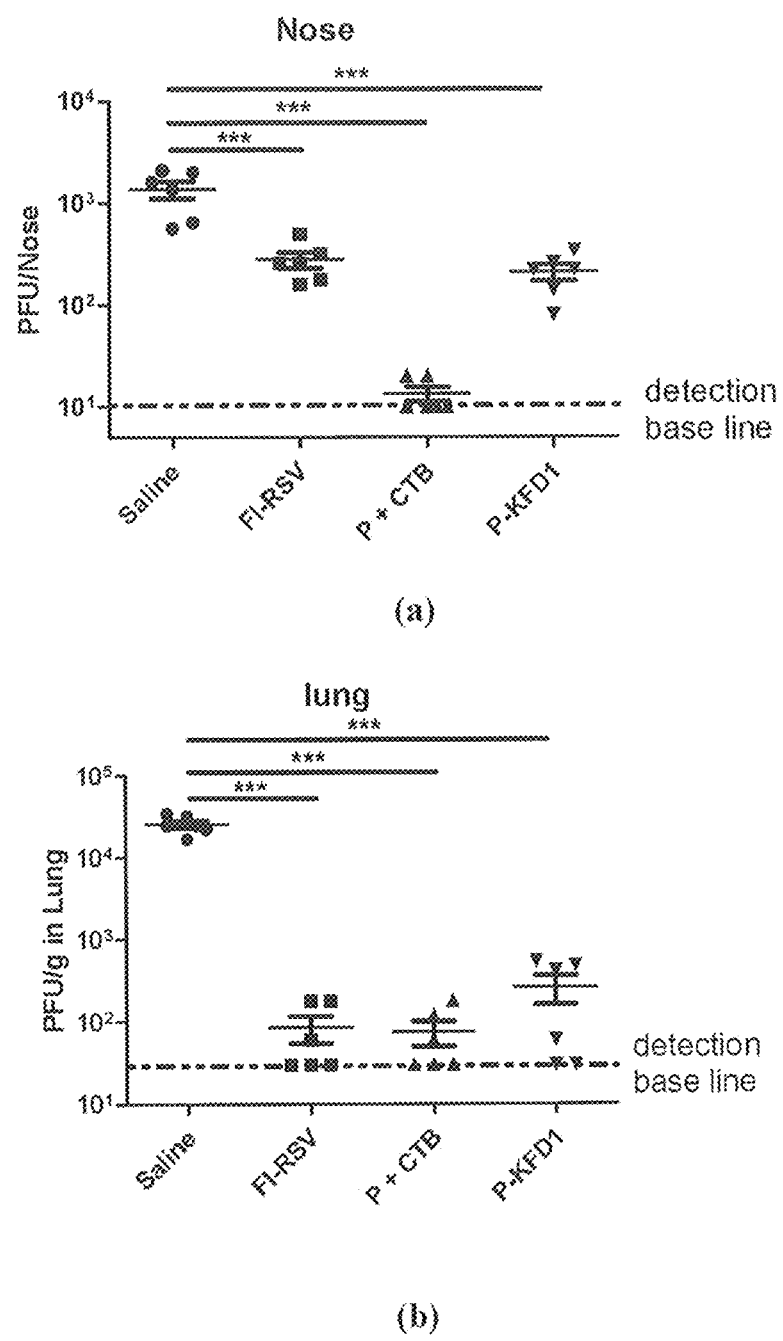
FIG. 5 provides graphs showing viral loads in nose or lung after challenge.

Referring now to FIG. 5, there are provided graphs showing viral loads in (a) nose or (b) lung after challenge.

Figure 6:
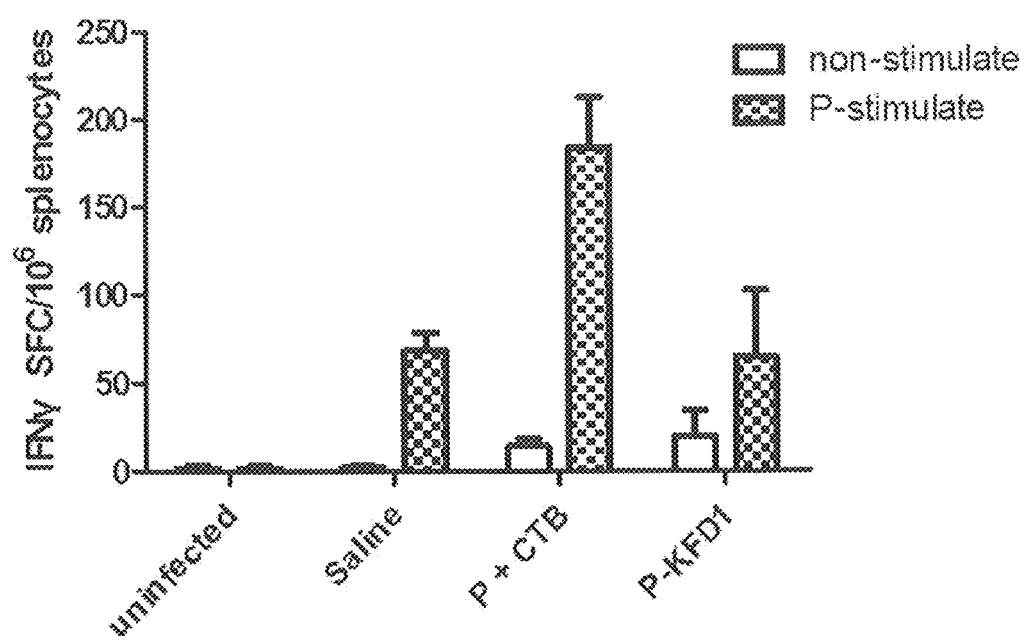
FIG. 6 provides a graph showing the P-specific T cell responses.

Referring now to FIG. 6, there is provided a graph showing the P-specific T cell responses. The group of P+CTB immunization showed significant T cell response; in contrast, the group of P-KDF1 immunization showed insignificant T cell response.

Figure 7:
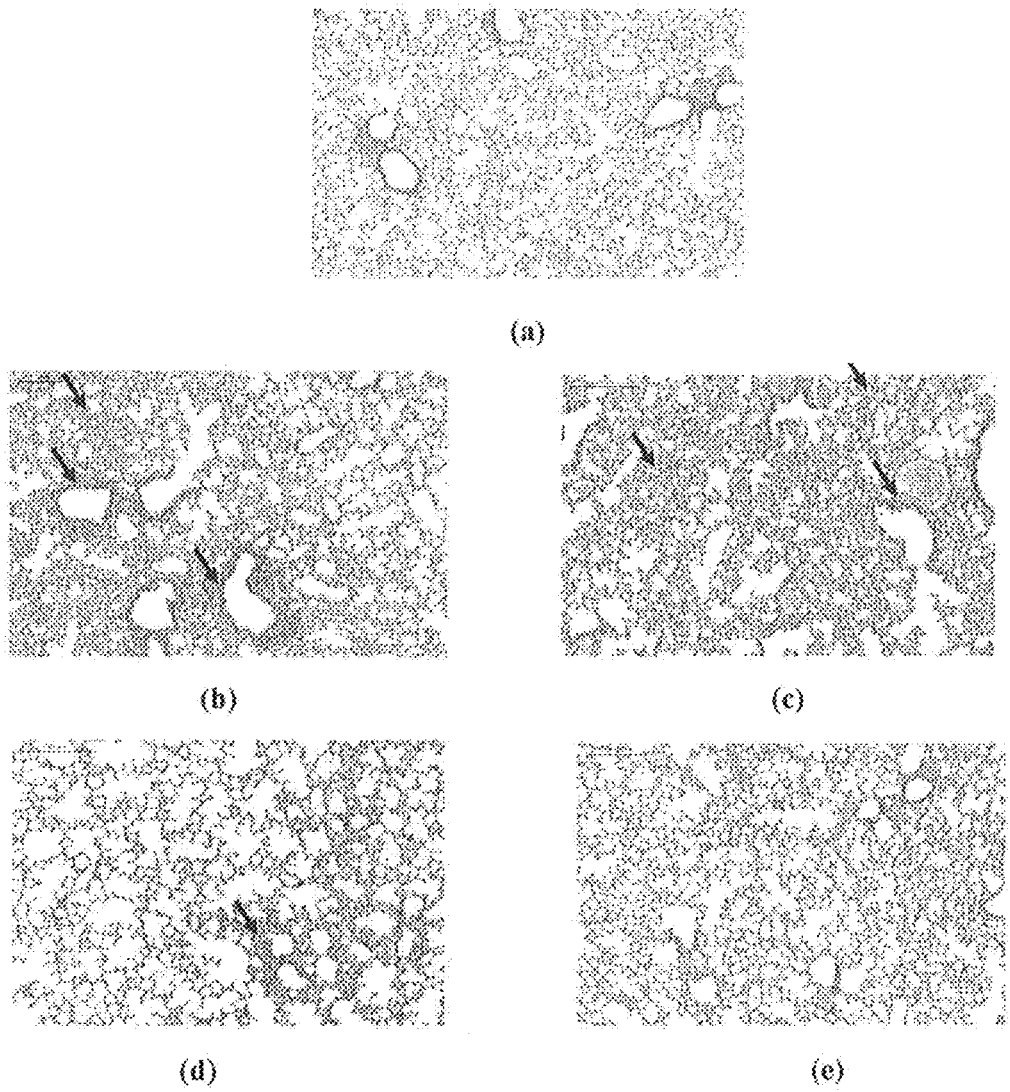
FIG. 7 provides a panel of pictures showing the lung tissues: (a) normal and uninfected; (b) control group immunized with saline and infected with RSV; (c) FI-RSV immunized group infected with RSV; (d) P+CTB immunized group infected with RSV; and (e) P–KFD1 immunized group infected with RSV.

Referring now to FIG. 7, there is provided a panel of pictures showing the lung tissues: (a) normal and uninfected, (b) control group immunized with saline and infected with RSV; (c) FI-RSV immunized group infected with RSV; (d) P+CTB immunized group infected with RSV; and (e) P-KFD1 immunized group infected with RSV. All sections from immunized groups were from mice at day 7 post infection. The saline and FI-RSV groups showed a large number of interstitial pneumonia and bronchitis; the P+CTB group had a large number of lymphocytic infiltrations; and surprisingly the P-KFD1 group had no apparent pathological lesions.

Figure 8:
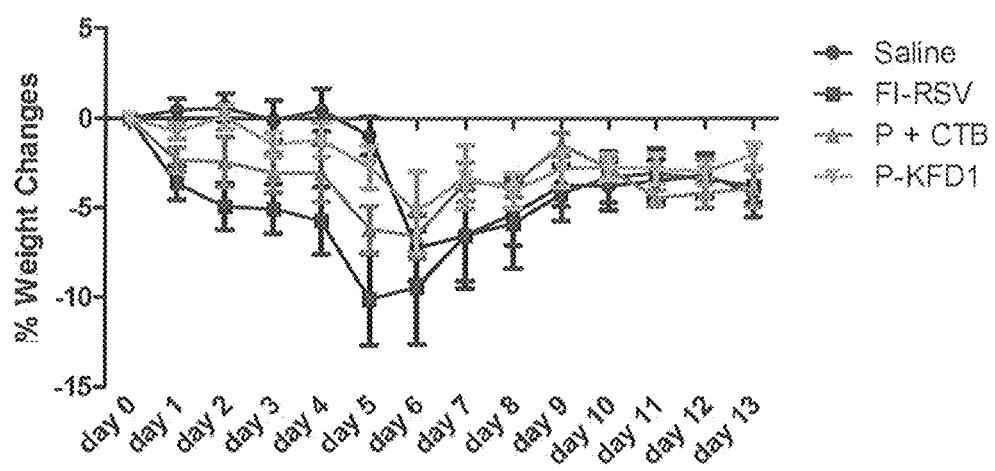
FIG. 8 is a graph showing the weight changes after challenge.

Referring now to FIG. 8, there is provided a graph showing the weight changes after challenge. The P-KFD1 group showed evident less weight loss than the other groups.

Referring now to FIG. 9, there are provided graphs: (a) showing the correlation of inspiratory resistance (RI) with different concentrations of methacholine (MCH); and (b) showing the correlation of expiratory resistance (RE) with different concentrations of methacholine (MCH) in different groups after challenge. The P-KFD1 group showed better RI and RE values than the FI-RSV and P+CTB groups.

Figure 10:
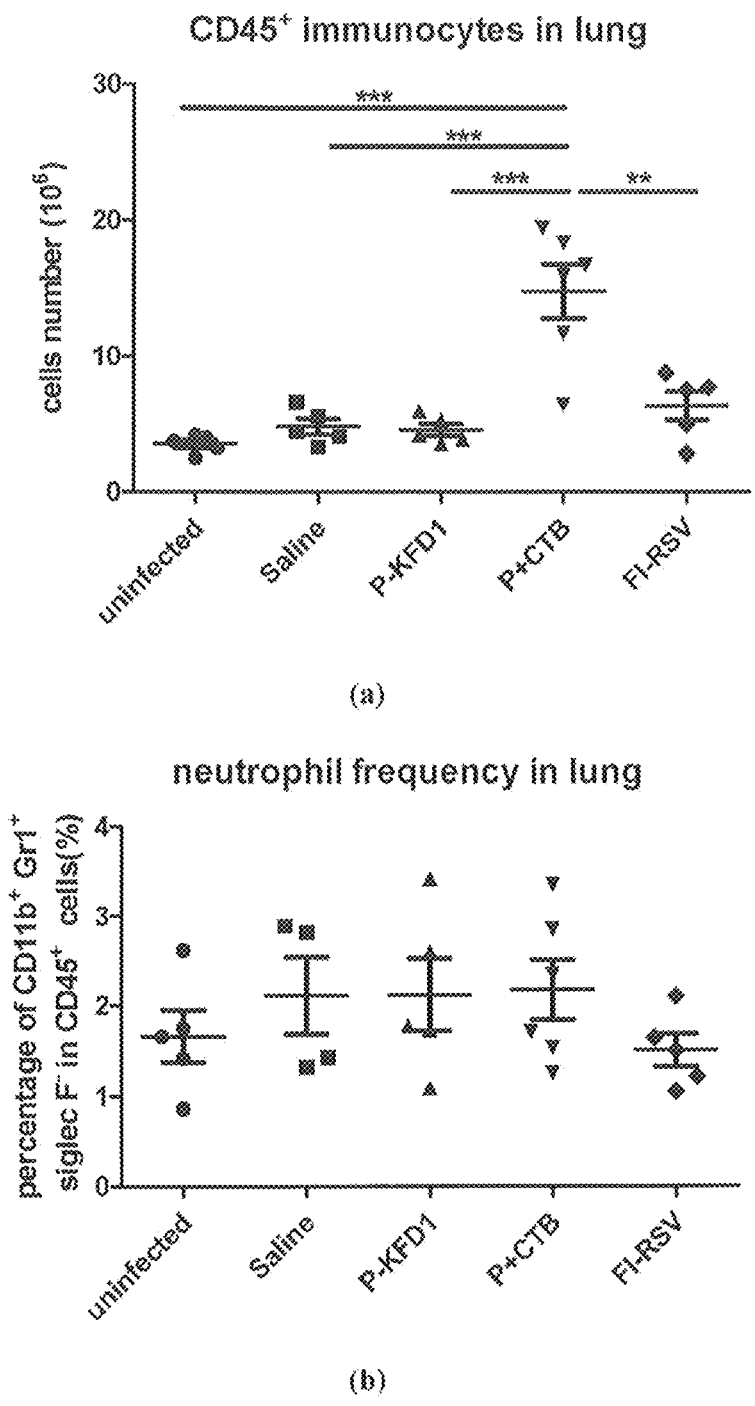
FIG. 10 provides graphs showing lymphocyte infiltration into lung tissues at day 8 post challenge; (a) immunocyte numbers; (b) neutrophil frequency in lung; (c) eosinophil frequency in lung; and (d) recruited macrophage frequency in lung.

Referring now to FIG. 10, there are provided graphs showing lymphocyte infiltration into lung tissues at day 8 post challenge; (a) immunocyte numbers; (b) neutrophil frequency in lung; (c) eosinophil frequency in lung; and (d) recruited macrophage frequency in lung P-KFD1 group has less immunocyte infiltration than P+CTB group. P+KFD1 group showed no significant infiltrated eosinophils and macrophages.

While the present invention has been described with reference to particular embodiments, it will be understood that the embodiments are illustrative and that the invention scope is not limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

REFERENCES

Cullen L M, Blanco J C, Morrison T G. Cotton rat immune responses to virus-like particles containing the pre-fusion form of respiratory syncytial virus fusion protein. *J Transl Med.* 2015 Nov. 5; 13:350.

Delgado M F[1], Coviello S, Monsalvo A C, Melendi G A, Hernandez J Z, Batalle J P, Diaz L, Trento A, Chang H Y, Mitzner W, Ravetch J, Melero J A, Irusta P M, Polack F P. Lack of antibody affinity maturation due to poor Toll-like receptor stimulation leads to enhanced respiratory syncytial virus disease. *Nat Med.* 2009 January; 15(1):3441.

Green C A, Scarselli E, Sande C J, Thompson A J, de Lara C M, Taylor K S, Haworth K, Del Sorbo M, Angus B, Siani L, Di Marco S, Traboni C, Folgori A, Colloca S, Capone S, Vitelli A, Cortese R, Klenerman P, Nicosia A, Pollard A J. Chimpanzee adenovirus- and MVA-vectored respiratory syncytial virus vaccine is safe and immunogenic in adults. *Sci Transl Med.* 7:300ra126 (2015)

Groothuis J R, King S J, Hogerman D A, Paradiso P R, Simoes E A. Safety and immunogenicity of a purified f protein respiratory syncytial virus (pfp-2) vaccine in seropositive children with bronchopulmonary dysplasia. *The Journal of infections diseases.* 1998; 177(2):467-469.

Hägglund S, Hu K, Blodörn K, Makabi-Parwu B, Gaillard A L, Ellencrona K, Chevret D, Hellman L, Bengtsson K L, Riffault S, Taylor G, Valarcher J F, Eléouët J F. Characterization of an experimental vaccine for bovine respiratory syncytial virus. *Clin Vaccine Immunol.* 21: 997-1004 (2014).

Kim K. H., Lee Y. T., Hwang H. S., Kwon Y. M., Jung Y. J., Lee Y., Lee J. S., Lee Y. N., Park S., Kang S. M. Alum adjuvant enhances protection against respiratory syncytial virus but exacerbates pulmonary inflammation in modulating multiple innate and adaptive immune cells *PLOS ONE.* 10: e0139916 (2015).

Lee S, Quan F S, Kwon Y, Sakamoto K, Kang S M, Compans R W, Moore M L. Additive protection induced by mixed a virus-like particles presenting respiratory syncytial virus fusion or attachment glycoproteins. *Antiviral Res.* 2014 November; 111:129-35.

Schepens B[1], Sedeyn K[2], Vande Ginste L[2], De Baets S[2], Schotsaert M[2], Roose K[2], Houspie L[3], Van Ranst M[3], Gilbert B[4], van Rooijen N[5], Fiers W[2], Piedra P[6], Saelens X[1]. Protection and mechanism of action of a novel human respiratory syncytial virus vaccine candidate based on the extracellular domain of small hydrophobic protein. *EMBO Mol Med.* 2014 Oct. 8; 6(II);1436-54.

Yang K. and S. M. Varga. Mucosal vaccines against respiratory syncytial virus. *Curr Opin Virol.* 6:78-84 (2014).

What is claimed is:

1. A respiratory syncytial virus (RSV) vaccine comprising a recombinant fusion protein antigen; wherein the recombinant fusion protein antigen comprises:
   a phosphoprotein (P) moiety, wherein the P moiety is a polypeptide that shares at least 90% identify to the polypeptide represented by SEQ ID NO 2 or SEQ ID NO 4; and
   a flagellin moiety, wherein the flagellin moiety is a polypeptide that shares at least 90% identity to the polypeptide represented by SEQ ID NO 8;
   where the P moiety and flagellin moiety are covalently coupled so as to form a linear polypeptide.

2. The RSV vaccine of claim 1, wherein the P moiety is a polypeptide that shares at least 98% identity to the polypeptide represented by SEQ ID NO 2 or SEQ ID NO 4; and wherein the flagellin moiety is a polypeptide that shares at least 98% identity to the polypeptide represented by SEQ ID NO 8.

3. The RSV vaccine of claim 1, wherein the P moiety is a polypeptide that shares at least 99% identity to the polypeptide represented by SEQ ID NO 2 or SEQ ID NO 4; and wherein the flagellin moiety is a polypeptide that shares at least 99% identity to the polypeptide represented by SEQ ID NO 8.

4. The RSV vaccine of claim 1, wherein the P moiety is a polypeptide represented by SEQ ID NO 2 or SEQ ID NO 4; and therein the flagellin moiety is a polypeptide represented by SEQ ID NO 8.

5. The RSV vaccine of claim 1, wherein the recombinant fusion protein antigen further comprises a first linker coupling the P moiety and flagellin moiety; wherein the first linker is an amino acid or a peptide of two to fifteen amino acids.

6. The RSV vaccine of claim 1, wherein the recombinant fusion protein antigen further comprises a purification tag for facilitating the purification of the recombinant fusion protein antigen, wherein the purification tag is disposed at either the N-terminal or C-terminal of the recombinant fusion protein antigen.

7. The RSV vaccine of claim 6, wherein the purification tag is composed of six histidine residues.

8. The RSV vaccine of claim 6, wherein the recombinant protein antigen further comprises a second linker linearly coupling the purification tag with the P moiety or flagellin moiety.

9. The RSV vaccine of claim 8, wherein the second linker is a cleavable linker that is composed of an amino acid or a sequence of amino acids which can be cleaved chemically or enzymatically at its C-terminal.

10. The RSV vaccine of claim 1, wherein the recombinant fusion protein antigen is represented by SEQ ID NO 10.

* * * * *

SEQUENCE LISTING

```
<160> NUMBER OF SEQ ID NOS: 16

<210> SEQ ID NO 1
<211> LENGTH: 813
<212> TYPE: DNA
<213> ORGANISM: respiratory syncytial virus

<400> SEQUENCE: 1
atgggcagca gccatcatca tcatcatcac agcagcggcc tggtgccgcg cggcagccat      60
atggctagca tggaaaagtt cgcgcctgaa ttccatggag aagatgcaaa caacagggct     120
actaaattcc tagaatcaat aaagggcaaa ttcacatcac ccaaagatcc caagaaaaaa     180
gatagtatca tatctgtcaa ctcaatagat atagaagtaa ccaaagaaag ccctataaca     240
tcaaattcaa ctattatcaa cccaacaaat gagacagatg atactgcagg gaacaagccc     300
aattatcaaa gaaaacctct agtaagtttc aaagaagacc ctacaccaag tgataatccc     360
```

```
ttttctaaac tatacaaaga aaccatagaa acatttgata acaatgaaga agaatccagc    420
tattcatacg aagaaataaa tgatcagaca aacgataata taacagcaag attagatagg    480
attgatgaaa aattaagtga aatactagga atgcttcaca cattagtagt ggcaagtgca    540
ggacctacat ctgctcggga tggtataaga gatgccatgg ttggtttaag agaagaaatg    600
atagaaaaaa tcagaactga agcattaatg accaatgaca gattagaagc tatggcaaga    660
ctcaggaatg aggaaagtga aaagatggca aagacacat cagatgaagt gtctctcaat     720
ccaacatcag agaaattgaa caacctattg gaagggaatg atagtgacaa tgatctatca    780
cttgaagatt ttaagcttgc gggcgcactc gag                                 813
```

```
<210> SEQ ID NO 2
<211> LENGTH: 271
<212> TYPE: PRT
<213> ORGANISM: respiratory syncytial virus

<400> SEQUENCE: 2

Met Gly Ser Ser His His His His His Ser Gly Leu Val P

<213> ORGANISM: respiratory syncytial virus

<400> SEQUENCE: 3

```
atggaaaagt tcgcgcctga attccatgga gaagatgcaa acaacagggc tactaaattc     60
ctagaatcaa taaagggcaa attcacatca cccaaagatc ccaagaaaaa agatagtatc    120
atatctgtca actcaataga tatagaagta accaaagaaa gccctataac atcaaattca    180
actattatca acccaacaaa tgagacagat gatactgcag ggaacaagcc caattatcaa    240
agaaaacctc tagtaagttt caaagaagac cctacaccaa gtgataatcc cttttctaaa    300
ctatacaaag aaaccataga aacatttgat aacaatgaag aagaatccag ctattcatac    360
gaagaaataa atgatcagac aaacgataat ataacagcaa gattagatag gattgatgaa    420
aaattaagtg aaatactagg aatgcttcac acattagtag tggcaagtgc aggacctaca    480
tctgctcggg atggtataag agatgccatg gttggtttaa gagaagaaat gatagaaaaa    540
atcagaactg aagcattaat gaccaatgac agattagaag ctatggcaag actcaggaat    600
gaggaaagtg aaaagatggc aaaagacaca tcagatgaag tgtctctcaa tccaacatca    660
gagaaattga acaacctatt ggaagggaat gatagtgaca atgatctatc acttgaagat    720
ttt                                                                  723
```

<210> SEQ ID NO 4
<211> LENGTH: 241
<212> TYPE: PRT
<213> ORGANISM: respiratory syncytial virus

<400> SEQUENCE: 4

```
Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
    50                  55                  60

Pro Thr Asn Glu Thr Asp Asp Thr Ala Gly Asn Lys Pro Asn Tyr Gln
65                  70                  75                  80

Arg Lys Pro Leu Val Ser Phe Lys Glu Asp Pro Thr Pro Ser Asp Asn
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175

Met Ile Glu Lys Ile Arg Thr Glu Ala Leu Met Thr Asn Asp Arg Leu
            180                 185                 190

Glu Ala Met Ala Arg Leu Arg Asn Glu Glu Ser Glu Lys Met Ala Lys
        195                 200                 205

Asp Thr Ser Asp Glu Val Ser Leu Asn Pro Thr Ser Glu Lys Leu Asn
    210                 215                 220

Asn Leu Leu Glu Gly Asn Asp Ser Asp Asn Asp Leu Ser Leu Glu Asp
225                 230                 235                 240

Phe

<210> SEQ ID NO 5
<211> LENGTH: 834
<212> TYPE: DNA
<213> ORGANISM: Artificial Sequence
<220> FEATURE:
<223> OTHER INFORMATION: Recombinant P protein with His tag

<400> SEQUENCE: 5

```
atgggcagca gccatcatca tcatcatcac agcagcggcc tggtgccgcg cggcagccat      60
atggctagca tggaaaagtt cgcgcctgaa ttccatggag aagatgcaaa caacagggct     120
actaaattcc tagaatcaat aaagggcaaa ttcacatcac ccaagatcc caagaaaaaa      180
gatagtatca tatctgtcaa ctcaatagat atagaagtaa ccaagaaag ccctataaca      240
tcaaattcaa ctattatcaa cccaacaaat gagacagatg atactgcagg gaacaagccc     300
aattatcaaa gaaaacctct agtaagtttc aaagaagacc ctacaccaag tgataatccc     360
ttttctaaac tatacaaaga aaccatagaa acatttgata caatgaaga gaatccagc       420
tattcatacg aagaaataaa tgatcagaca acgataata taacagcaag attagatagg      480
attgatgaaa aattaagtga aatactagga atgcttcaca cattagtagt ggcaagtgca     540
ggacctacat ctgctcggga tggtataaga gatgccatgg ttggtttaag agaagaaatg     600
atagaaaaaa tcagaactga agcattaatg accaatgaca gattagaagc tatggcaaga     660
ctcaggaatg aggaaagtga aaagatggca aagacacat cagatgaagt gtctctcaat      720
ccaacatcag agaaattgaa caacctattg gaagggaatg atagtgacaa tgatctatca     780
cttgaagatt ttaagcttgc gggcgcactc gagcaccacc accaccacca ctga           834
```

<210> SEQ ID NO 6
<211> LENGTH: 277
<212> TYPE: PRT
<213> ORGANISM: Artificial Sequence
<220> FEATURE:
<223> OTHER INFORMATION: Recombinant RSV P protein with His tag

<400> SEQUENCE: 6

Met Gly Ser Ser His His His His His His Ser Ser Gly Leu Val Pro
1               5                   10                  15

Arg Gly Ser His Met Ala Ser Met Glu Lys Phe Ala Pro Glu Phe His
                20                  25                  30

Gly Glu Asp Ala Asn Asn Arg Ala Thr Lys Phe Leu Glu Ser Ile Lys
            35                  40                  45

Gly Lys Phe Thr Ser Pro Lys Asp Pro Lys Lys Asp Ser Ile Ile
        50                  55                  60

Ser Val Asn Ser Ile Asp Ile Glu Val Thr Lys Glu Ser Pro Ile Thr
65                  70                  75                  80

Ser Asn Ser Thr Ile Ile Asn Pro Thr Asn Glu Thr Asp Asp Thr Ala
                85                  90                  95

Gly Asn Lys Pro Asn Tyr Gln Arg Lys Pro Leu Val Ser Phe Lys Glu
            100                 105                 110

Asp Pro Thr Pro Ser Asp Asn Pro Phe Ser Lys Leu Tyr Lys Glu Thr
        115                 120                 125

Ile Glu Thr Phe Asp Asn Asn Glu Glu Glu Ser Ser Tyr Ser Tyr Glu

```
                130                 135                 140
Glu Ile Asn Asp Gln Thr Asn Asp Asn Ile Thr Ala Arg Leu Asp Arg
145                 150                 155                 160

Ile Asp Glu Lys Leu Ser Glu Ile Leu Gly Met Leu His Thr Leu Val
                165                 170                 175

Val Ala Ser Ala Gly Pro Thr Ser Ala Arg Asp Gly Ile Arg Asp Ala
            180                 185                 190

Met Val Gly Leu Arg Glu Glu Met Ile Glu Lys Ile Arg Thr Glu Ala
                195                 200                 205

Leu Met Thr Asn Asp Arg Leu Glu Ala Met Ala Arg Leu Arg Asn Glu
            210                 215                 220

Glu Ser Glu Lys Met Ala Lys Asp Thr Ser Asp Val Ser Leu Asn
225                 230                 235                 240

Pro Thr Ser Glu Lys Leu Asn Asn Leu Leu Glu Gly Asn Asp Ser Asp
                245                 250                 255

Asn Asp Leu Ser Leu Glu Asp Phe Lys Leu Ala Gly Ala Leu Glu His
            260                 265                 270

His His His His His
        275

<210> SEQ ID NO 7
<211> LENGTH: 801
<212> TYPE: DNA
<213> ORGANISM: Artificial Sequence
<220> FEATURE:
<223> OTHER INFORMATION: Recombinant flagellin KFD1

<400> SEQUENCE: 7
atggcacaag tcattaatac caacagcctc tcgctgatca ctcaaaataa tatcaacaag    60
aaccagtctg cgctgtcgag ttctatcgag cgtctgtctt ctggcttgcg tattaacagc   120
gcgaaggatg acgcagcggg tcaggcgatt gctaaccgtt tcacctctaa cattaaaggc   180
ctgactcagg cggcccgtaa cgccaacgac ggtatctccg ttgcgcagac caccgaaggc   240
gcgctgtccg aaatcaacaa caacttacag cgtgtgcgtg aactgacggt acaggccact   300
accggtacta actctgagtc tgatctgtct tctatccagg acgaaattaa atcccgtctg   360
gatgaaattg accgcgtatc tggtcagacc cagttcaacg gcgtgaacgt gctggcaaaa   420
aatggctcca tgaaaatcca ggttggcgca atgataaacc agactatcac tatcgatctg   480
aagcagattg atgctaaaac tcttggcctt gatgctagcg ctacgacgac ggatccgctg   540 aaaagcgctgg acgatgctat cgcatctgta gacaaattcc gttcttccct cggtgcggtg   600
caaaaccgtc tggattccgc ggttaccaac ctgaacaaca ccactaccaa cctgtctgaa   660
gcgcagtccc gtattcagga cgccgactat gcgaccgaag tgtccaatat gtcgaaagcg   720
cagatcatcc agcaggccgg taactccgtg ttggcaaaag ctaaccaggt accgcagcag   780
gttctgtctc tgctgcaggg t                                              801

<210> SEQ ID NO 8
<211> LENGTH: 267
<212> TYPE: PRT
<213> ORGANISM: Artificial Sequence
<220> FEATURE:
<223> OTHER INFORMATION: Recombinant flagellin KFD1

<400> SEQUENCE: 8

Met Ala Gln Val Ile Asn Thr Asn Ser Leu Ser Leu Ile Thr Gln Asn
1               5                   10                  15
```

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
 50                  55                  60

Ala Arg Asn Ala Asn Asp Gly Ile Ser Val Ala Gln Thr Thr Glu Gly
 65                  70                  75                  80

Ala Leu Ser Glu Ile Asn Asn Leu Gln Arg Val Arg Glu Leu Thr
                85                  90                  95

Val Gln Ala Thr Thr Gly Thr Asn Ser Glu Ser Asp Leu Ser Ser Ile
            100                 105                 110

Gln Asp Glu Ile Lys Ser Arg Leu Asp Glu Ile Asp Arg Val Ser Gly
            115                 120                 125

Gln Thr Gln Phe Asn Gly Val Asn Val Leu Ala Lys Asn Gly Ser Met
 130                 135                 140

Lys Ile Gln Val Gly Ala Asn Asp Asn Gln Thr Ile Thr Ile Asp Leu
145                 150                 155                 160

Lys Gln Ile Asp Ala Lys Thr Leu Gly Leu Asp Ala Ser Ala Thr Thr
                165                 170                 175

Thr Asp Pro Leu Lys Ala Leu Asp Asp Ala Ile Ala Ser Val Asp Lys
            180                 185                 190

Phe Arg Ser Ser Leu Gly Ala Val Gln Asn Arg Leu Asp Ser Ala Val
        195                 200                 205

Thr Asn Leu Asn Asn Thr Thr Thr Asn Leu Ser Glu Ala Gln Ser Arg
    210                 215                 220

Ile Gln Asp Ala Asp Tyr Ala Thr Glu Val Ser Asn Met Ser Lys Ala
225                 230                 235                 240

Gln Ile Ile Gln Gln Ala Gly Asn Ser Val Leu Ala Lys Ala Asn Gln
                245                 250                 255

Val Pro Gln Gln Val Leu Ser Leu Leu Gln Gly
            260                 265

<210> SEQ ID NO 9
<211> LENGTH: 1629
<212> TYPE: DNA
<213> ORGANISM: Artificial Sequence
<220> FEATURE:
<223> OTHER INFORMATION: Recombinant P-KFD1

<400> SEQUENCE: 9
atgggcagca gccatcatca tcatcatcac agcagcggcc tggtgccgcg cggcagccat      60
atggctagca tggaaaagtt cgcgcctgaa ttccatggag aagatgcaaa caacagggct     120
actaaattcc tagaatcaat aaagggcaaa ttcacatcac ccaaagatcc caagaaaaaa     180
gatagtatca tatctgtcaa ctcaatagat atagaagtaa ccaaagaaag ccctataaca     240
tcaaattcaa ctattatcaa cccaacaaat gagacagatg atactgcagg gaacaagccc     300
aattatcaaa gaaaacctct agtaagtttc aaagaagacc ctacaccaag tgataatccc     360 tttttctaaac tatacaaaga aaccatgaaa acatttgata caatgaaga gaatccagc      420 tattcatacg aagaaataaa tgatcagaca acgataata taacagcaag attagatagg     480
attgatgaaa aattaagtga atactagga atgcttcaca cattagtagt ggcaagtgca     540
ggacctacat ctgctcggga tggtataaga gatgccatgg ttggtttaag agaagaaatg     600

-continued

| | |
|---|---|
| atagaaaaaa tcagaactga agcattaatg accaatgaca gattagaagc tatggcaaga | 660 |
| ctcaggaatg aggaaagtga aaagatggca aaagacacat cagatgaagt gtctctcaat | 720 |
| ccaacatcag agaaattgaa caacctattg gaagggaatg atagtgacaa tgatctatca | 780 |
| cttgaagatt tcgggcgcgc catggcacaa gtcattaata ccaacagcct ctcgctgatc | 840 |
| actcaaaata atatcaacaa gaaccagtct gcgctgtcga gttctatcga gcgtctgtct | 900 |
| tctggcttgc gtattaacag cgcgaaggat gacgcagcgg gtcaggcgat tgctaaccgt | 960 |
| ttcacctcta acattaaagg cctgactcag gcggcccgta acgccaacga cggtatctcc | 1020 |
| gttgcgcaga ccaccgaagg cgcgctgtcc gaaatcaaca caacttaca gcgtgtgcgt | 1080 |
| gaactgacgg tacaggccac taccggtact aactctgagt ctgatctgtc ttctatccag | 1140 |
| gacgaaatta aatcccgtct ggatgaaatt gaccgcgtat ctggtcagac ccagttcaac | 1200 |
| ggcgtgaacg tgctggcaaa aaatggctcc atgaaaatcc aggttggcgc aaatgataac | 1260 |
| cagactatca ctatcgatct gaagcagatt gatgctaaaa ctcttggcct tgatgctagc | 1320 |
| gctacgacga cggatccgct gaaagcgctg acgatgcta tcgcatctgt agacaaattc | 1380 |
| cgttcttccc tcggtgcggt gcaaaaccgt ctggattccg cggttaccaa cctgaacaac | 1440 |
| accactacca acctgtctga agcgcagtcc cgtattcagg acgccgacta tcgaccgaa | 1500 |
| gtgtccaata tgtcgaaagc gcagatcatc cagcaggccg gtaactccgt gttggcaaaa | 1560 |
| gctaaccagg taccgcagca ggttctgtct ctgctgcagg gtctcgagca ccaccaccac | 1620 |
| caccactga | 1629 |

<210> SEQ ID NO 10
<211> LENGTH: 542
<212> TYPE: PRT
<213> ORGANISM: Artificial Sequence
<220> FEATURE:
<223> OTHER INFORMATION: Recombinant P-KFD1

<400> SEQUENCE: 10

Met Gly Ser Ser His His His His His Ser Ser Gly Leu Val Pro
1               5                   10                  15

Arg Gly Ser His Met Ala Ser Met Glu Lys Phe Ala Pro Glu Phe His
            20                  25                  30

Gly Glu Asp Ala Asn Asn Arg Ala Thr Lys Phe Leu Glu Ser Ile Lys
        35                  40                  45

Gly Lys Phe Thr Ser Pro Lys Asp Pro Lys Lys Asp Ser Ile Ile
    50                  55                  60

Ser Val Asn Ser Ile Asp Ile Glu Val Thr Lys Glu Ser Pro Ile Thr
65 70 75 80

Ser Asn Ser Thr Ile Ile Asn Pro Thr Asn Glu Thr Asp Asp Thr Ala
85 90 95

Gly Asn Lys Pro Asn Tyr Gln Arg Lys Pro Leu Val Ser Phe Lys Glu
100 105 110

Asp Pro Thr Pro Ser Asp Asn Pro Phe Ser Lys Leu Tyr Lys Glu Thr
115 120 125

Ile Glu Thr Phe Asp Asn Asn Glu Glu Glu Ser Ser Tyr Ser Tyr Glu
130 135 140

Glu Ile Asn Asp Gln Thr Asn Asp Asn Ile Thr Ala Arg Leu Asp Arg
145 150 155 160

Ile Asp Glu Lys Leu Ser Glu Ile Leu Gly Met Leu His Thr Leu Val
165 170 175

Val Ala Ser Ala Gly Pro Thr Ser Ala Arg Asp Gly Ile Arg Asp Ala
            180                 185                 190

Met Val Gly Leu Arg Glu Glu Met Ile Glu Lys Ile Arg Thr Glu Ala
        195                 200                 205

Leu Met Thr Asn Asp Arg Leu Glu Ala Met Ala Arg Leu Arg Asn Glu
    210                 215                 220

Glu Ser Glu Lys Met Ala Lys Asp Thr Ser Asp Glu Val Ser Leu Asn
225                 230                 235                 240

Pro Thr Ser Glu Lys Leu Asn Asn Leu Leu Glu Gly Asn Asp Ser Asp
                245                 250                 255

Asn Asp Leu Ser Leu Glu Asp Phe Gly Arg Ala Met Ala Gln Val Ile
            260                 265                 270

Asn Thr Asn Ser Leu Ser Leu Ile Thr Gln Asn Asn Ile Asn Lys Asn
        275                 280                 285

Gln Ser Ala Leu Ser Ser Ser Ile Glu Arg Leu Ser Ser Gly Leu Arg
    290                 295                 300

Ile Asn Ser Ala Lys Asp Asp Ala Ala Gly Gln Ala Ile Ala Asn Arg
305                 310                 315                 320

Phe Thr Ser Asn Ile Lys Gly Leu Thr Gln Ala Ala Arg Asn Ala Asn
                325                 330                 335

Asp Gly Ile Ser Val Ala Gln Thr Thr Glu Gly Ala Leu Ser Glu Ile
            340                 345                 350

Asn Asn Asn Leu Gln Arg Val Arg Glu Leu Thr Val Gln Ala Thr Thr
        355                 360                 365

Gly Thr Asn Ser Glu Ser Asp Leu Ser Ser Ile Gln Asp Glu Ile Lys
    370                 375                 380

Ser Arg Leu Asp Glu Ile Asp Arg Val Ser Gly Gln Thr Gln Phe Asn
385                 390                 395                 400

Gly Val Asn Val Leu Ala Lys Asn Gly Ser Met Lys Ile Gln Val Gly
                405                 410                 415

Ala Asn Asp Asn Gln Thr Ile Thr Ile Asp Leu Lys Gln Ile Asp Ala
            420                 425                 430

Lys Thr Leu Gly Leu Asp Ala Ser Ala Thr Thr Thr Asp Pro Leu Lys
        435                 440                 445

Ala Leu Asp Asp Ala Ile Ala Ser Val Asp Lys Phe Arg Ser Ser Leu
    450                 455                 460

Gly Ala Val Gln Asn Arg Leu Asp Ser Ala Val Thr Asn Leu Asn Asn
465                 470                 475                 480

Thr Thr Thr Asn Leu Ser Glu Ala Gln Ser Arg Ile Gln Asp Ala Asp
                485                 490                 495

Tyr Ala Thr Glu Val Ser Asn Met Ser Lys Ala Gln Ile Ile Gln Gln
            500                 505                 510

Ala Gly Asn Ser Val Leu Ala Lys Ala Asn Gln Val Pro Gln Gln Val
        515                 520                 525

Leu Ser Leu Leu Gln Gly Leu Glu His His His His His His
    530                 535                 540

<210> SEQ ID NO 11
<211> LENGTH: 31
<212> TYPE: DNA
<213> ORGANISM: Artificial Sequence
<220> FEATURE:
<223> OTHER INFORMATION: Primer P up with NheI

<400> SEQUENCE: 11

```
tatagctagc atggaaaagt tcgcgcctga a                              31

<210> SEQ ID NO 12
<211> LENGTH: 27
<212> TYPE: DNA
<213> ORGANISM: Artificial Sequence
<220> FEATURE:
<223> OTHER INFORMATION: Primer P downstream with Hind III site

<400> SEQUENCE: 12
attaaagctt aaaatcttca agtgata                                   27

<210> SEQ ID NO 13
<211> LENGTH: 31
<212> TYPE: DNA
<213> ORGANISM: Artificial Sequence
<220> FEATURE:
<223> OTHER INFORMATION: Primer for pET28a P upstream with Nhe1 site

<400> SEQUENCE: 13
tatagctagc atggaaaagt tcgcgcctga a                              31

<210> SEQ ID NO 14
<211> LENGTH: 33
<212> TYPE: DNA
<213> ORGANISM: Artificial Sequence
<220> FEATURE:
<223> OTHER INFORMATION: Primer for pET28a P downstream with AscI site

<400> SEQUENCE: 14
atttggcgcg cccgaaatct tcaagtgata gat                            33

<210> SEQ ID NO 15
<211> LENGTH: 32
<212> TYPE: DNA
<213> ORGANISM: Artificial Sequence
<220> FEATURE:
<223> OTHER INFORMATION: Primer for pET28a KF upstream with AscI site

<400> SEQUENCE: 15
atttggcgcg ccatggcaca agtcattaat ac                             32

<210> SEQ ID NO 16
<211> LENGTH: 28
<212> TYPE: DNA
<213> ORGANISM: Artificial Sequence
<220> FEATURE:
<223> OTHER INFORMATION: Primer for pET28a KF downstream with XhoI site

<400> SEQUENCE: 16
atatctcgag accctgcagc agagacag                                  28
```